United States Patent [19]

Delachapelle

[11] Patent Number: 4,670,223
[45] Date of Patent: Jun. 2, 1987

[54] APPARATUS FOR PRODUCING STERILE AIR FOR MEDICAL USE

[75] Inventor: Henri L. Delachapelle, Nantes, France

[73] Assignee: Le Masne S.A., France

[21] Appl. No.: 571,997

[22] Filed: Jan. 19, 1984

[30] Foreign Application Priority Data

Jan. 26, 1983 [FR] France ................................ 83-01156

[51] Int. Cl.⁴ .......................................... B01D 50/00
[52] U.S. Cl. ..................... 422/122; 422/169; 422/171; 422/4; 55/279; 55/316; 55/319; 55/323; 55/DIG. 17; 55/DIG. 25
[58] Field of Search ................. 422/4, 122, 169, 171; 55/30, 31, 33, 35, 76, 180, 279, 316, 389, 528, 525; 423/230, 242, 244–247; 237/65, 66; 165/110; 34/73, 74, 75, 79, 80, 82

[56] References Cited

U.S. PATENT DOCUMENTS

| | | | |
|---|---|---|---|
| 3,555,787 | 1/1971 | Lustig | 55/316 |
| 3,905,783 | 7/1975 | Winter et al. | 55/31 |
| 3,966,407 | 6/1976 | Zuckerberg et al. | 422/4 |
| 3,989,461 | 11/1976 | Skocypec et al. | 422/111 |
| 4,162,289 | 7/1979 | Gomez et al. | 422/4 |
| 4,314,828 | 2/1982 | Saito et al. | 55/179 |
| 4,331,455 | 5/1982 | Sato | 55/31 |
| 4,428,756 | 1/1984 | Iniotakis | 55/158 |
| 4,430,306 | 2/1984 | Namba et al. | 55/31 |
| 4,448,757 | 5/1984 | Barnwell et al. | 422/113 |
| 4,468,239 | 8/1984 | Frantz | 55/162 |
| 4,478,800 | 10/1984 | Van der Wal et al. | 423/230 |

OTHER PUBLICATIONS

Health Technical Memorandum, Piped Medical Compressed Air and Medical Vacuum Installations, May 1972, pp. 19–22.

*Primary Examiner*—David L. Lacey
*Attorney, Agent, or Firm*—Darby & Darby

[57] ABSTRACT

Apparatus for producing sterile air suitable for being administered to intensive-care patients in hospitals using atmospheric air. The medical-grade air is free of gaseous contaminants and germs, at a cost substantially lower than when such air is prepared by mixing pure nitrogen with pure oxygen.

Atmospheric air is compressed through at least one dry-piston compressor, condensing water vapor out of the compressed air through expansion into a buffer tank, filtering out dust particles down to micron size in a prefilter, drying the air through an adsorption desiccator unit and eliminating gaseous contaminants through an adsorption-desorption unit. A second dust filter is provided for trapping any dust released from the adsorption units. Biological contaminants, such as viruses and bacteria, are eliminated by flowing through a sequence of three biological filters of the coalescence type, and finally through a cold sterilizing unit.

17 Claims, 1 Drawing Figure

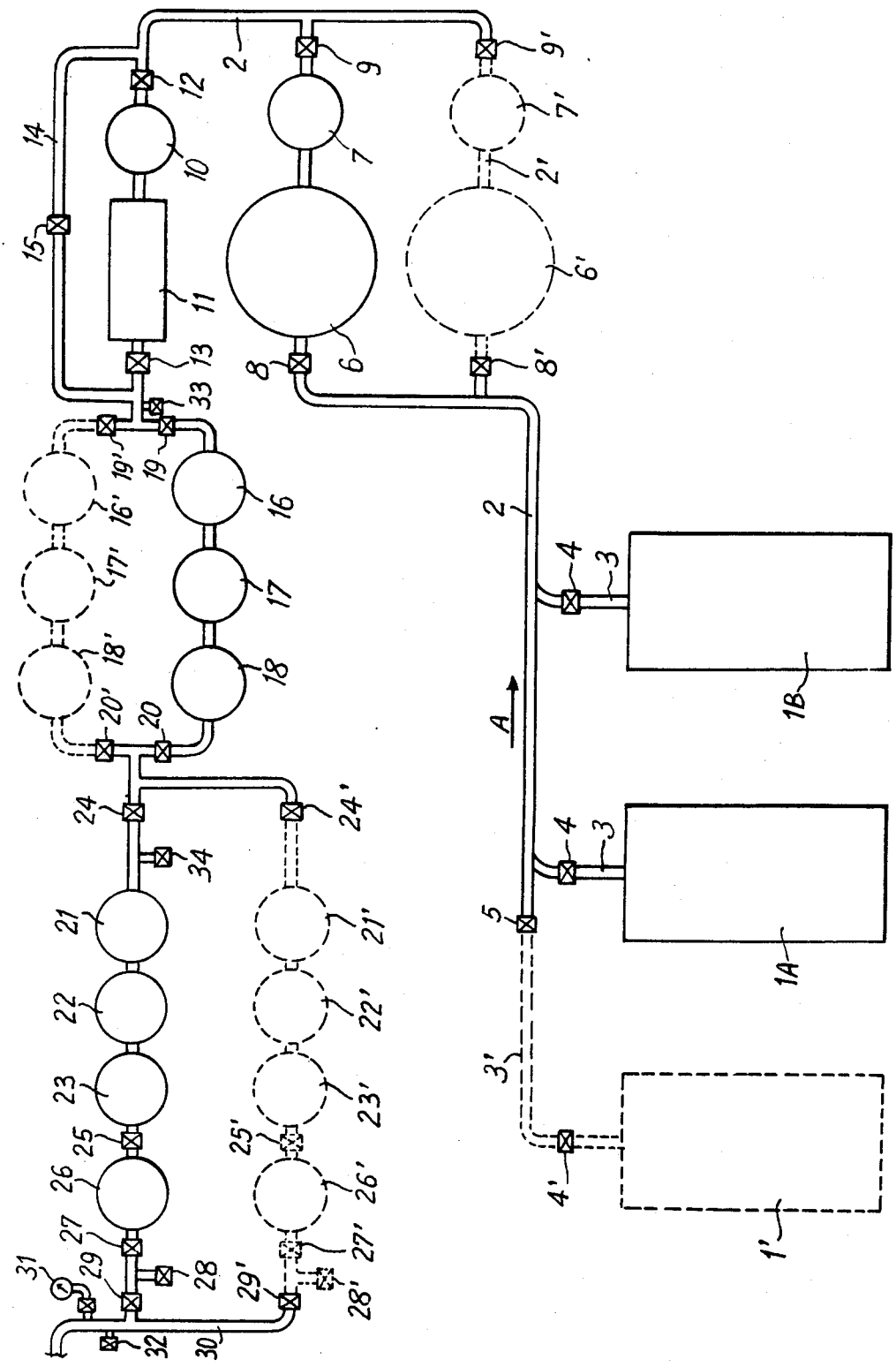

APPARATUS FOR PRODUCING STERILE AIR FOR MEDICAL USE

This invention relates to a method and apparatus for producing medical-grade air appropriate for being administered to patients undergoing intensive care, such as for reanimation. This medical air should, as far as possible, be completely free of any impurity and of any germ.

The main purpose of this invention is to provide sterile air for medical use, starting from atmospheric air, while obtaining the requested degree of purity, particularly as regards the complete elimination of noxious gaseous contaminants and germs.

A further object of the invention is to achieve the production of medical air at a cost which will be substantially lower than the production cost of sterile air obtained by mixing pure nitrogen with pure oxygen.

Yet another object of the invention is to take avail of the heat produced by the compression of air for supplying thermal energy to a catalytic operation in which carbon monoxide is eliminated by being converted to dioxide.

BACKGROUND OF THE INVENTION

Heretofore, conventional methods for treating atmospheric air do not appear to have achieved a sufficient degree of purification for rendering such treated air appropriate for being administered to patients.

For this reason, medical-grade air is now preferably produced by mixing pure nitrogen with pure oxygen. However, the production cost of this method is relatively high.

The purpose of this invention is therefore to produce sterile air for medical use by purifying atmospheric air, achieving the required degree of purity, particularly in respect of complete elimination of gaseous contaminants and of germs such as bacteria, while maintaining the production cost at a level appreciably below the cost of the now prevalent method in which pure nitrogen is mixed with pure oxygen for obtaining sterile air.

SUMMARY OF THE INVENTION

The method according to this invention comprises the steps of compressing atmospheric air by means of at least one dry-piston compressor, and subjecting this air to the following treatment stages:
  one stage of water vapor condensation,
  one first stage of dust filtration, down to micron size,
  a desiccation stage,
  a stage for the elimination of gaseous contaminants,
  a second stage of dust filtration, also down to micron size,
  a stage for the elimination of bacteria,
this method being characterized, according to the invention, by the feature of providing for the desiccation stage and for the gas removal stage two adsorption-desorption filters containing an active product of the same nature, the gas removal process taking place downstream of the desiccating operation, while the desiccator unit contains a larger quantity of the said active product than the gas removal unit.

Characteristically, the unit designed for removing gaseous contaminants should contain approximately fifty percent more active product than the desiccator unit.

According to another feature of this invention, the elimination of bacteria is carried out in three successive stages, as the compressed air is caused to flow sequentially through three coalescence filters, the filtration threshold of which decreases gradually down to 0.01 micron, while a cold sterilizing stage is provided downstream of said three filters.

The method of this invention is further characterized in that the filtering operations are carried out with a low velocity of air flow through all the filters, down to the second one of the coalescence filters provided for eliminating bacteria, while subsequently accelerating the air flow rate through the third and last coalescence filter and through the cold sterilizing stage.

More particularly, a feature of the invention consists in setting the air flow velocity through the last coalescence filter of the bacteria eliminating stage and through the cold sterilizing stage at a value exceeding by a factor comprised between 1.5 and 3 the flow velocity through the other processing stages.

Another feature of the invention consists in providing an additional stage for eliminating carbon monoxide, whenever it is present in the atmospheric air being treated, by converting said monoxide to dioxide through a catalytic reaction preferably carried out at a temperature in the range from 120° C. to 130° C., the catalytic agent being preferably in the form of platinum-coated pellets made either of metal or of a refractory material, and having a rough surface.

According to the invention, the active product in the desiccation stage and in the stage for eliminating gaseous contaminants is a compound of metal oxides with potassium, sodium and Mg silicates.

According to a further feature, the filtering material for the elimination of bacteria through the coalescence filters is formed of boro-silicate glass fibers coated with a sheath of porous plastic material.

For achieving the highest possible degree of deodorization of the treated air, there will advantageously be added to the last one of the coalescence filters an absorption device using active carbon.

As to the cold sterilizing stage, this is preferably provided with a filtering device for retaining dust particles released from upstream stages, this device being preferably in the form of a cartridge of boro-silicate glass fibers having been subjected to a hydrophobic treatment.

BRIEF DESCRIPTION OF THE DRAWING

Further features and advantages of this invention will appear from the following detailed description, with reference to the appended drawing showing diagrammatically a preferred embodiment of an apparatus for carrying out the method of the invention.

DETAILED DESCRIPTION OF THE INVENTION

Referring to the single FIGURE of the drawing, which illustrates an apparatus for treating atmospheric air so as to obtain medical-grade sterile air, according to this invention, this apparatus comprises:
  at least one dry compressor,
  a buffer tank for smoothing out the air flow from the compressor and for condensing water vapor,
  one first dust filter,
  a desiccator,
  a desulfurizer unit,
  a second dust filter, a microbiological pre-filter,
a microbiological separator,
a microbiological deodorizer,
a cold sterilizer.

In addition to the above devices, the apparatus will also comprise, whenever the air being treated is likely to be contaminated with carbon monoxide, a catalytic device for converting this monoxide to dioxide, followed by a combined heat-exchanger and condenser. Both these devices are connected to the outlet of the first dust filter, upstream of the desiccator.

Summarily, the apparatus is composed of five categories of devices corresponding to five critical stages of the method according to the invention, namely:
1. Air compression.
2. preliminary treatment.
3. Carbon monoxide treatment.
4. Desiccation and elimination of gaseous contaminants.
5. Hyperfiltration and sterilization.

These five stages will now be described in detail, the direction of air flow being indicated by an arrow A

1. Air compression

The air compression stage comprises two reciprocating compressors 1A and 1B. These compressors are preferably of the dry-piston type. Compressors of this kind require no lubrication, since their connecting rods and piston axes are mounted on bearings which are greased for a lifetime, and the piston rings are made of a self-lubricating PTFE(poltetratfluorothylene)-based material.

The compressed air is therefore free of any oil originating from the compressor operation.

A standby compressor 1', shown in dotted lines, is installed in parallel with the two compressors 1A and 1B. It may be used when maintenance or repair work is carried out on either of main compressors 1A and 1B.

Compressors 1A and 1B are connected to a main air duct 2 by means of two branch lines 3, each of which is provided with a valve 4.

Similarly, the standby compressor 1' is connected to duct 2 by a branch line 3' with a valve 4'. A further valve 5 is placed at the junction of the branch line 3' with duct 2.

2. Preliminary treatment

Duct 2 leads compressed air to a buffer tank 6 which smooths out pulsations from the reciprocating compressors 1A and 1B, and also fills the purpose of extracting at least a part of the water present in the air. As the compressed air enters tank 6, it becomes cooled through expansion, so that droplets of water present in the air will condense on the tank walls.

Downstream of tank 6 is placed a dust filter 7, capable of retaining dust particles down to the micron size. Appropriate filters for this purpose are for instance coalescence filters of a known type comprising a cartridge of alumina having been vitrified at 1100° C.

This section of the apparatus may be isolated by means of inlet valve 8 and outlet valve 9. Similarly to the compressors, a standby equipment (shown in dotted lines) is provided in parallel. It comprises a bypass duct 2', a tank 6', a dust filter 7' and two valves 8' and 9'.

3. Carbon monoxide treatment

Air released from filter 7 reaches a catalytic converter device 10 in which carbon monoxide CO is oxidized into dioxide $CO_2$. This catalytic device contains a metallic oxidizer heated by an electric resistor to a temperature in the range of about 120° C. to 130° C., so as to achieve a complete oxidization of carbon monoxide for converting it to dioxide $CO_2$.

The metallic oxidizing agent may advantageously be in the form of platinum-coated pellets made either of metal or of a refractory material. Preferably, these pellets have a rough surface so as to increase their exchange area.

Since air becomes heated to 120°–130° C. when flowing through the catalytic converter device 10, it has to be cooled back to ambient temperature before being subjected to the desiccation treatment and to the elimination of gaseous contaminants, as described under Stage 4 hereinafter.

This cooling operation is carried out downstream of catalytic converter 10 in a combined exchanger-condenser or cooler 11 of a known type, which should preferably present a substantial heat-exchange area. A suitable cooler may for instance be formed of a copper tube in a zig-zag configuration, on which are soldered large aluminum fins, the cooler being further equipped with a fan.

According to a modified embodiment, the catalytic converter 10 and its heat-exchanger 11 may be placed between the desiccator 16 and the desulfurizer 17 which will be described hereinafter.

After flowing through this desulfurizer 17, the air is completely free of carbon dioxide $CO_2$. If, however, it is desired for specific applications that the treated air should contain a small amount of $CO_2$, it will then be appropriate to place the catalytic converter 10 and its exchanger 11 downstream of the desulfurizer 17, just ahead of the battery of coalescence filters 21, 22, 23 of the bacterial filtration stage which will be described subsequently. Thus, $CO_2$ contained in the atmospheric air is eliminated by the desulfurizer, while the required supply of additional $CO_2$ is provided by the catalytic converter device 10 and its exchanger 11 through conversion of CO contained in the atmospheric air. In this case, the catalytic converter device 10 and its exchanger are preferably placed between the second dust filter 18 and the first bacterial filter 21. Two valves 12 and 13 are placed on the inlet to the catalytic converter 10 and on the outlet of the condenser 11, respectively.

On another hand, a bypass line 14 in parallel with duct 2 and controlled by valve 15 makes it possible to feed the air directly to the desiccator 16 and to the desulfurizer 17, when this air does not contain any carbon monoxide.

A further standby circuit, not shown on the diagram, may also be provided, which will include a catalytic converter and a cooler.

4. Desiccation and extraction of gaseous contaminants

Air leaving cooler 11 is thoroughly dried as it flows through a desiccator 16 operating on the adsorption-desorption principle. The active product in this unit is a compound of metal oxides with silicates of potassium, sodium and magnesium. Desiccator 16 is formed of two pressurized cylinders, one of which is operative while the other is regenerating. An automatic switching device is provided for periodically inverting the operation of the cylinders. During the regenerating (desorption) phase, the cylinder concerned is heated by an electric resistor at about 180° C. Water molecules having been adsorbed are released and are blown away towards a drain valve by a very slight blast of dry air coming from the operative cylinder. This desiccating operation is needed for eliminating from the air stream any water vapor which would not have been extracted by condensation in buffer tank 6 during the preliminary treatment.

Downstream of the desiccator 16 is placed a device 17 for the elimination of gaseous contaminants, generally described as a "desulfurizer", the purpose of which is to remove sulfurous anhydride, hydrogen sulfide, nitrogen peroxide, carbon dioxide, hydrocarbon vapors, fluorine, chlorine, mercaptans, lead tetraethyl or tetramethyl and all other unwanted gases which are usually present in the atmosphere of towns.

The desulfurizer 17 is similar to the desiccator 16. It operates on the same adsorption-desorption principle, and its active agent is similarly a compound of metal oxides with potassium, sodium and magnesium silicates. However, on the one hand, the proportions in the composition of the product are different, and on the other hand the amount of active product is greater in the desulfurizer than in the desiccator. Use can advantageously be made in the desulfurizer of the active agent the amount being approximately 50 percent more than in the desiccator.

The adsorbing material in desulfurizer 17 is effective for deodorizing the air while simultaneously eliminating gaseous contaminants. Desorption is carried out at a temperature of 220° C., higher than the 180° C. desorption temperature of the desiccator, 16.

A second dust filter 18, identical to the primary filter 7, is placed directly downstream of desulfurizer 17. The function of this second filter is to screen out any dust particles which might result from the erosion of adsorbing materials used in devices 16 and 17. Two valves 19 and 20 are provided respectively upstream of dryer 16 and downstream of the secondary filter 18. A standby unit (shown in dotted lines) is installed in parallel with the above devices. It also comprises a desiccator 16', a desulfurizer 17', a filter 18, and two valves 19' and 20'.

Air coming out of this section of the apparatus is dry and has been cleared of all undesirable mineral particles. There remains the need to remove biological contaminants (viruses, microbes) through the hyperfiltration and sterilization sequence.

5. Hyperfiltration and sterilization

By hyperfiltration is meant filtration down to a size limit of approximately one hundredth of a micron (i.e. $10^{-8}$ meter). For this operation, there is provided a battery of three coalescence filters 21, 22, 23 of a known type, the filtrating element of which is formed of a mat of borosilicate glass fibers coated with a porous plastic sheath, with a density of glass fibers which determines a decreasing filtration threshold from one filter to the next. Thus, in the first filter 21, the filtration threshold is 0.6 micron, whereas in the second and third filters 22, 23, the threshold is 0.01 micron. The third filter 23 further includes an absorption device in which active carbon is effective, not only for retaining bacteria, but also for finishing the deodorizing effect of the above-described desulfurizer unit 17. Two valves 24, 25 are provided respectively on the inlet and outlet of the hyperfiltration stage.

A cold sterilizer 26 of a known type is placed upstream of valve 24. It comprises a cartridge of borosilicate glass fibers which have received an hydrophobic treatment, this cartridge being in a stainless steel frame. A valve 27 is placed on the outlet of sterilizer 26, so that by closing valves 25 and 27 the sterilizer may be isolated for receiving a periodical sterilization treatment. Downstream of valve 27 are found a sampling valve 28, a general cut-off valve 29, the outlet duct 30 with a pressure gauge 31 and a safety pressure sensor 32. The sampling valve makes it possible to check the air purity as it leaves sterilizer 26 and thus the overall effectiveness of the apparatus. The safety pressure sensor 32 will automatically close down the operation of the apparatus whenever the delivery pressure in outlet duct 30 drops below a predetermined value. Further sampling valves 33 and 34 similar to valve 28 are installed respectively on the outlet of the exchanger-condenser 11 for checking correct operation of the catalytic converter 10 and on the inlet to filter 21 for checking correctiom operation of the desiccator and desulfurizer units.

A standby unit is also provided in parallel with the hyperfiltration and sterilization stage, comprising three filters 21', 22', 23', a sterilizer 26', valves 24', 25', 27', 29' and a sampling valve 28'.

The outlet duct 30 is connected in a conventional manner to the air distribution piping network of the hospital or nursing home. This outlet duct may advantageously be provided with suitable equipment (not shown) for filling storage cylinders with purified air.

Whereas in the above-described system the carbon monoxide catalytic converter 10 is located between the primary dust filter 7 and the desiccator 16, another advantageous embodiment consists in placing this converter device between the compressor 1 and the buffer tank 6, thus taking avail of the heat content of the air leaving the compressors for substantially reducing the heat input required for the catalytic action.

According to a further advantageous modification, filtration is carried out with a slow velocity of air flow through every filter until the second coalescence filter 22 in the bacterial filtration stage, and the air flow is then accelerated through the third filter 23 and the sterilizer 26. In this case, the filter containing active carbon is preferably placed in the second position rather than in the third one. This makes it possible to avoid a too rapid plugging of the filtering units located upstream of the third bacterial filter 23, and thus to achieve a more effective prefiltration than when the flow velocity is constant throughout the whole filtering line. This procedure also provides for a longer contact time of the air being treated with the deodorizing component of the second coalescence filter 22 in the bacterial filtering stage, and will thus achieve a more thorough deodorizing action.

Finally, the fact of using a low velocity of air flow through the major part of the overall system brings about a very substantial diminution of pressure drop through the filters.

However, the air flow velocity through the last coalescence filter 23 and through the sterilizer 26 should preferably be from one and a half to three times faster than through the rest of the system. A simple way to obtain a low velocity of the air flow through the filters placed upstream of the last coalescence filter 23 and the sterilizer 26, and therefore to obtain an acceleration of the air flow through these last two units, consists in providing an oversize passage area for each of the devices installed upstream of the last two above-mentioned units 23 and 26.

What is claimed is:

1. Apparatus for producing sterile air comprising:

at least one compressor having a dry piston for producing an air flow stream through said apparatus in a first downstream direction, at least one buffer tank connected to and in fluid communication with said at least one compressor for regulating the air flow stream from said at least one compressor by at least smoothing pulsations in the air flow stream and for extracting water in the stream by condensation, a first dust removal filter connected to and in fluid communication with said at least one buffer tank, an adsorption-desorption desiccator connected to and in fluid communication with said first dust removal filter, an adsorption-desorption means connected to and in fluid communication with said adsorption-desorption desiccator for eliminating undesired gases in the air flow stream produced by said compressor, a second dust removal filter connected to and in fluid communication with said adsorption-desorption means, a series of first, second and third coalescence filters having sequentially decreasing filtration thresholds ranging down to 0.01 micron, said first, second and third coalescence filters being serially connected to and in fluid communication with said second dust removal filter for eliminating bacteria, and a cold sterilizing unit connected to and in fluid communication with said serially connected coalescence filters.

2. Apparatus according to claim 1, wherein the desiccator and the gas adsorption-desorption means each include a compound of metal oxides with silicates of potassium, sodium and magnesium, the quantity of said compound in the gas adsorption-desorption means being larger than the quantity in the desiccator.

3. Apparatus according to claim 2, in which the gas adsorption-desorption means contains approximately 50 percent more of said compound than the desiccator.

4. Apparatus according to claim 1, in which the coalescence filters arranged in series for the elimination of bacteria include a filtering material of boro-silicate glass fibers coated with a sheath of porous plastic material.

5. Apparatus according to claim 4, wherein said third coalescence filter includes an active carbon absorption device.

6. Apparatus according to claim 5, wherein said cold sterilizing unit includes a filtering device comprising a cartridge of boro-silicate glass fibers having been subjected to hydrophobic treatment and maintained in a stainless steel frame.

7. Apparatus according to claim 6, further comprising means for converting carbon monoxide to carbon dioxide, said converting means being connected between and in fluid communication with at least said at least one compressor and said gas adsorption-desorption means.

8. Apparatus according to claim 1, further comprising means for converting carbon monoxide to carbon dioxide, said converting means being connected between and in fluid communication with at least said at least one compressor and said gas adsorption-desorption means.

9. Apparatus according to claim 8, in which the converter means is connected between said at least one compressor and said dessicator.

10. Apparatus according to claim 8 wherein said converter means further comprises a catalytic device containing a metallic oxidizer to be heated to a temperature ranging from 120° C. to 130° C., and means for heating said oxidizer to said temperature range, said apparatus further comprising a heat exchanger and a condenser unit, connected to and in fluid communication with said converter means, for cooling the air flow stream produced by said compressor.

11. Apparatus according to claim 10, in which the metallic oxidizer in said catalytic device comprises platinum-coated metal pellets.

12. Apparatus according to claim 11, in which said pellets have a rough surface.

13. Apparatus according to claim 12, in which said dust removal filters include a cartridge of alumina having been vitrified at approximately 1100° C.

14. Apparatus according to claim 13, wherein said second sequential coalescence filter further comprises an absorption device containing active carbon.

15. Apparatus according to claim 14, in which said first and second sequential coalescence filters have an oversize passage area therethrough with respect to the passage area through said third coalescence filter, so as to cause an air flow velocity through said third coalescence filter which is one and one-half to three times faster than the flow velocity through said first and second filters when said compressor produces the air flow through said apparatus.

16. Apparatus according to claim 10, wherein said metallic oxidizer in said catalytic device comprises platinum-coated pellets of a refractory material.

17. Apparatus according to claim 16, in which said pellets have a rough surface.

* * * * *